March 9, 1976
E. N. SWANE
CYPRESS TREE
Filed Jan. 9, 1975
Plant Pat. 3,839
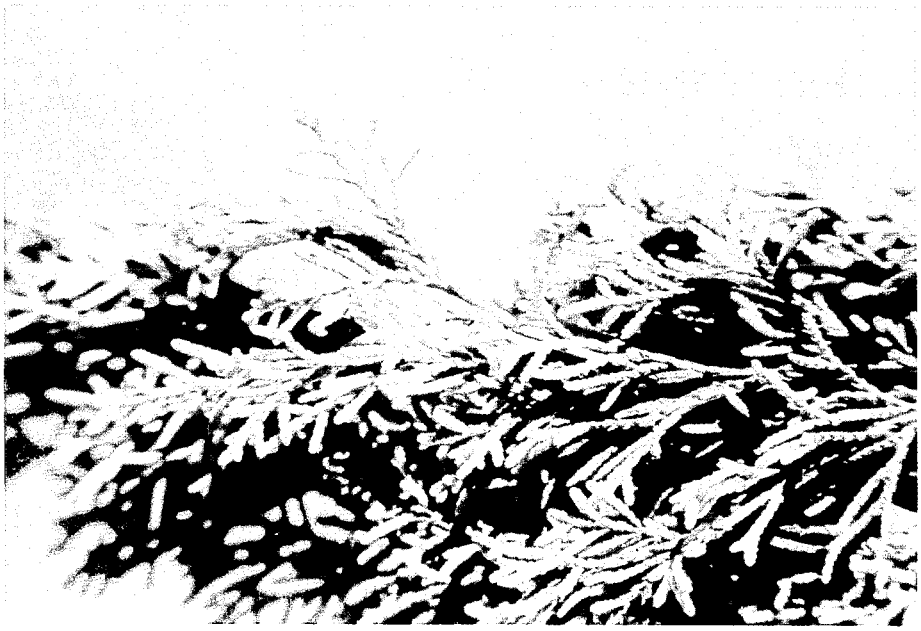
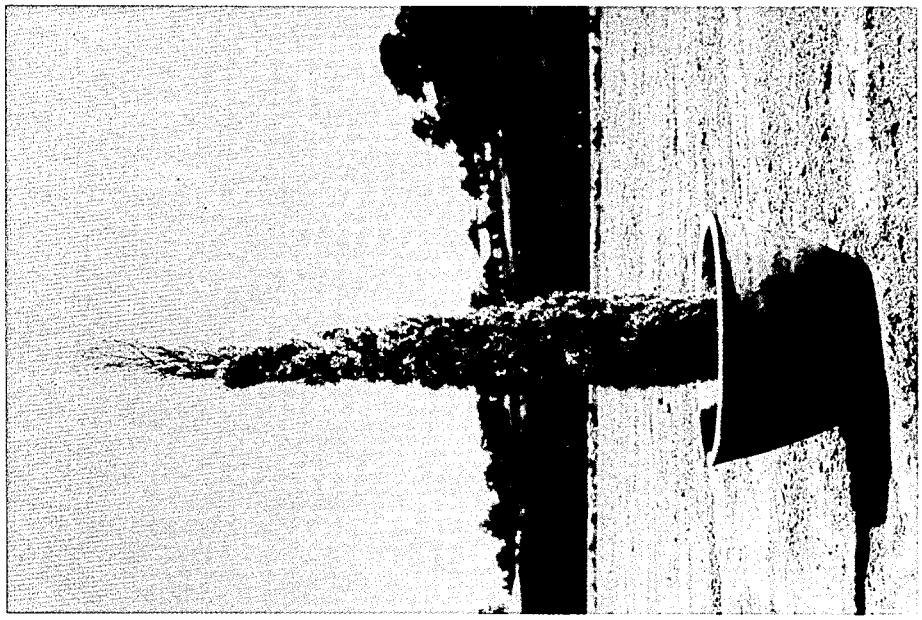

United States Patent

Plant Pat. 3,839
Patented Mar. 9, 1976

1

3,839
CYPRESS TREE

Edgar Norman Swane, Ermington, New South Wales, Australia, assignor to Swane Bros. Pty. Ltd., Dural, New South Wales, Australia Filed Jan. 9, 1975, Ser. No. 539,766
Int. Cl. A01h 7/00
U.S. Cl. Plt.—50 1 Claim The present invention relates to a new and distinct variety of cypress tree of the species botanically known as *Cupressus sempervirens stricta*, which was discovered by me as a selected natural seedling of an unnamed and unpatented variety of *Cupressus sempervirens stricta* of unknown parentage growing in my cultivated nursery located at Ermington, N.S.W., Australia.

While growing a block of cypress trees in my nursery aforesaid, my attention was attracted to several seedlings among those trees which bore bright yellow foliage contrary to the normal dark green foliage of all the other trees that were typical of the species *Cupressus sempervirens stricta*. I carefully preserved the new seedlings and kept them under close observation for a number of years and found that their bright yellow foliage remained very stable. In due course, I selected the best and asexually reproduced the same by cuttings taken therefrom, as performed under my direction and supervision in my nursery aforementioned. The progeny derived from these cuttings and from subsequent propagations through several generations consistently came true with respect to the unusual bright yellow color of the foliage. My prolonged observations and field tests of the new seedling and its progeny have convinced me that it represents a new and distinct variety which is generally typical of the species *Cupressus sempervirens stricta* except for its foliage color, as evidenced by the following unique combination of principal characteristics which are outstanding in the new seedling and distinguish it from all other varieties of cypress trees of which I am aware:

(1) A very slender, compact, upright and uniformly narrow-columnar habit of growth, with the apex of the tree usually consisting of a single leader shoot forming a long, tapering, erect point;
(2) An unusual bright golden yellow foliage color; and
(3) Good hardiness.

The accompanying drawing shows a typical tree specimen, as well as a close-up view of its typical foliage, as depicted in color as nearly true as it is reasonably possible to make the same in an illustration of this character.

Since the characteristics of my new seedling, except for its foliage color, generally mostly conform to those of the species *Cupressus sempervirens stricta* which are well-known, a detailed description of the new variety is not necessary herein, but for convenience, the following brief description thereof is given, with color terminology in accordance with Koster's Color Guide, except where general color terms of ordinary dictionary significane are obvious:

PARENTAGE: A natural seedling of an unnamed variety of the species *Cupressus sempervirens stricta*.

2

PROPAGATION: Holds its distinguishing characteristics through succeeding propagations by cuttings.

LOCALITY WHERE GROWN AND OBSERVED: Ermington, N.S.W., Australia.

TREE: Medium size; upright; very slender, compact and uniformly narrow-columnar, with apex usually consisting of a single leader shoot forming a long tapering erect point.

Trunk—Slender. Bark—Peels off in curled flakes; closely and shallowly fissured toward base of trunk only; color—from bright reddish brown to dull grey.

Branches—Erect and extending at a very acute angle to the trunk. Main branches—Straight or very slightly zig-zagging; intervals between side branches mostly from about 6 mm. to 10 mm. Branchlets—Dense and crowded, with strong tendency to be arranged in one plane in each ultimate branchlet system, but with branchlet systems arranged in varying planes forming a bushy appearance; ultimate branching systems occurring at intervals of mostly 2 mm. to 4 mm., with ultimate branchlets up to 20 mm. long, mostly gently curved and having a diameter of about 0.8 mm. to 1.0 mm. Leaves—Mostly borne on main branches in opposite pairs, with those of successive pairs being identical in shape and size, about 5 mm. to 6 mm. long, shortly acuminate, with apex diverging very slightly from branch; leaves of branchlets borne in opposite pairs and arranged in four identical rows and being about 0.7 mm. to 1.0 mm. long and about 0.6 mm. wide, diverging from axis at an angle of about 35° to 45°; ovate-elliptic in outline; dorsal surface strongly curved and with elongated, shallow, darker colored pit (resin gland) extending along most of its length in median position; apex obtuse and hooded. Color—Brownish green at first, with green upper portion changing at about 5 cm. from apex to pale red-brown and later to dull grey; leaves of branchlets which are still growing vigorously are lemon-yellow at apex, changing to pale yellowish-green within about 5 mm. of apex. General color tonality—From near Primrose Yellow, Plate No. 6 to near Indian Yellow, Plate No. 8.

HARDINESS: Good.

I claim:

1. A new and distinct variety of cypress tree of the species botanically known as *Cupressus sempervirens stricta*, substantially as herein shown and described, characterized particularly as to novelty by a very slender, compact, upright and uniformly narrow-columnar habit of growth, with the apex of the tree usually consisting of a single leader shoot forming a long, tapering, erect point, an unusual bright golden yellow foliage color and good hardiness.

No references cited.

ROBERT E. BAGWILL, Primary Examiner